US011006894B2

(12) United States Patent
Hollopeter et al.

(10) Patent No.: US 11,006,894 B2
(45) Date of Patent: May 18, 2021

(54) PRESSURE ULCER RISK MAPPING METHOD

(71) Applicant: American Sterilizer Company, Mentor, OH (US)

(72) Inventors: Michael Hollopeter, Kirtland, OH (US); Richard P. Nardo, Highland Heights, OH (US); Sohrab Soltani, Charleston, SC (US)

(73) Assignee: American Sterilizer Company, Mentor, OH (US)

( * ) Notice: Subject to any disclaimer, the term of this patent is extended or adjusted under 35 U.S.C. 154(b) by 265 days.

(21) Appl. No.: 15/210,331

(22) Filed: Jul. 14, 2016

(65) Prior Publication Data

US 2018/0014774 A1 Jan. 18, 2018

(51) Int. Cl.
*A61B 5/00* (2006.01)
*A61B 5/11* (2006.01)
(Continued)

(52) U.S. Cl.
CPC ............ *A61B 5/447* (2013.01); *A61B 5/1036* (2013.01); *A61B 5/1114* (2013.01);
(Continued)

(58) Field of Classification Search
CPC ..... A61B 5/447; A61B 5/1116; A61B 5/1036; A61B 5/1114; A61B 5/7275;
(Continued)

(56) References Cited

U.S. PATENT DOCUMENTS

| 2006/0058624 A1 | 3/2006 | Kimura | 600/407 |
| 2011/0263950 A1 | 10/2011 | Larson et al. | 600/301 |

(Continued)

FOREIGN PATENT DOCUMENTS

WO WO 2011/113070 A1 9/2011

OTHER PUBLICATIONS

International Search Report and Written Opinion from corresponding International Patent Application No. PCT/US2017/031019, dated Aug. 3, 2017.
(Continued)

*Primary Examiner* — Rene T Towa
(74) *Attorney, Agent, or Firm* — Kusner & Jaffe

(57) ABSTRACT

A method is provided for continuously monitoring pressure ulcer risk for a patient positioned on a support surface. The support surface has an associated pressure sensing device for sensing instantaneous pressure at the support surface. The method includes acquiring pressure data from the pressure sensing device to generate a two-dimensional instantaneous pressure (IP) map indicative of instantaneous pressure at locations of the support surface. The method further includes acquiring a body position model using the two-dimensional IP map, where the body position model includes body parts that are respectively mapped to locations on a pressure ulcer risk map. An accumulated risk is determined in associated with each body part. The pressure ulcer risk map is displayed in accordance with the accumulated risk. Further, a current body position model is compared to a previous body position model to detect a position change of the patient on the support surface.

10 Claims, 13 Drawing Sheets

(51) Int. Cl.
- *A61B 5/103* (2006.01)
- *G16H 50/50* (2018.01)
- *G16H 50/30* (2018.01)
- *G16H 40/63* (2018.01)

(52) U.S. Cl.
CPC .......... *A61B 5/1116* (2013.01); *A61B 5/6892* (2013.01); *A61B 5/7275* (2013.01); *A61B 5/743* (2013.01); *G16H 40/63* (2018.01); *G16H 50/30* (2018.01); *G16H 50/50* (2018.01); *A61B 2562/0247* (2013.01)

(58) Field of Classification Search
CPC .................. A61B 5/6892; A61B 5/743; A61B 2562/0247; G06F 19/00
See application file for complete search history.

(56) References Cited

U.S. PATENT DOCUMENTS

| | | | |
|---|---|---|---|
| 2013/0006151 A1 | 1/2013 | Main et al. | 600/587 |
| 2015/0320352 A1 | 11/2015 | Ben Shalom et al. | A61B 5/447 |

OTHER PUBLICATIONS

Kosiak M., "Etiology of Decubitus Ulcers," Archives of Physical Medicine & Rehabilitation, 1959, 40(2):6269 [PMID: 13618101].

Reswick et al., "Experience at Rancho Los Amigos Hospital with Devices and Techniques to Prevent Pressure Sores," Bed Sore Biomechanics, pp. 301-310, 1976.

Linder-Ganz et al., "Mechanical compression-induced pressure sores in rat hindlimb: muscle stiffness, histology, and computational models," Journal of Applied Physiology, vol. 96, pp. 2034-2049, Feb. 6, 2004.

Linder-Ganz et al., "Pressure-time cell death threshold for albino rat skeletal muscles as related to pressure sore biomechanics," Journal of Biomechanics, vol. 39, pp. 2725-2732 (2006).

Sprigle et al., "Assessing evidence supporting redistribution of pressure for pressure ulcer prevention: A review," Journal of Rehabilitation Research & Development, U.S. Department of Veterans Affairs, vol. 48, No. 3, pp. 203-214, 2011.

Loerakker et al., "The effects of deformation, ischemia, and reperfusion on the development of muscle damage during prolonged loading," Journal of Applied Physiology, vol. 111, pp. 1168-1177, Jul. 14, 2011.

Cuddigan, et al., "Pressure Ulcers: Prevalence, Incidence, and Implications for the Future," National Pressure Ulcer Advisory Panel, Washington DC: NPUAP, 2012.

Office Action, dated Nov. 18, 2019, issued in corresponding Canadian Patent Application No. 3,028,088.

Office Action issued in corresponding Australian Patent Application No. 2017295131 dated Jul. 31, 2019.

PRESSURE ULCER RISK MAPPING METHOD

FIELD OF THE INVENTION

The present invention relates generally to the art of pressure ulcer risk mapping, and, more particularly, to methods for monitoring pressure ulcer risk and displaying pressure ulcer risk maps.

BACKGROUND OF THE INVENTION

Research shows that more than one million people develop hospital-acquired pressure ulcers each year, and 25% of these injuries are associated with the operating room (OR). Unique patient risk factors, coupled with complex positioning and long surgical procedures, place surgical patients at increased risk. The National Quality Forum considers Stage III or IV health care-acquired pressure injuries to be Serious Reportable Events.

A support pad is typically used to support and cushion a patient undergoing surgery. During surgery, patient tissue is in contact with a thin sheet that is subsequently in contact with the support pad. This exposes patient tissue to pressure at an interface with a surface of the support pad. Pressure ulcers are more likely to develop in tissue that is exposed to elevated interface pressure levels for prolonged periods of time.

A pressure sensing device is commonly positioned within a support pad, or on or under the support pad. The pressure sensing device includes sensing elements that sense the instantaneous interface pressure applied to the patient. Pressure data corresponding with the sensed instantaneous interface pressure is transmitted to a controller. The controller processes the pressure data for data storage and/or display. The pressure data is often displayed in the form of a pressure map for ease of interpretation.

Examples of such maps include instantaneous pressure (IP) maps or pressure ulcer risk (PUR) maps. IP maps illustrate instantaneous exposure of tissue to pressure. PUR maps illustrate the risk of pressure ulcer development in tissue that is exposed to elevated pressure levels over prolonged periods of time.

Prior to surgery, IP maps are intended to aid medical personnel in repositioning a patient on the support surface to avoid pressure ulcer development during surgery. During surgery, IP and PUR maps are intended to aid medical personnel in determining whether a patient is at risk of pressure ulcer development and whether the patient should be repositioned to avoid such risk. After surgery, IP and PUR maps are intended to aid medical personnel in the tailoring of post-operative care and the identification of pressure ulcers that were formed during surgery.

However, since IP maps illustrate instantaneous exposure of tissue to pressure, medical personnel cannot use IP maps to determine how tissue has been or will be impacted by exposure to elevated pressure levels over prolonged periods of time. As a result, any initial repositioning of the patient based on IP maps may be inaccurate.

Furthermore, existing PUR mapping systems commonly illustrate multiple categories or levels of pressure ulcer risk simultaneously, such as, for example, high risk, medium risk, low risk, and no risk. Without extensive training on how to identify PUR from such maps, medical personnel may reposition the patient earlier or later than necessary. This may result in unnecessary surgical delay, increased surgical costs, and unintended development of pressure ulcers during surgery.

In addition, in existing PUR mapping systems the repositioning of a patient during surgery will trigger a PUR map to be reset, thereby eliminating all of the previously identified locations of PUR on the PUR map. However, repositioning of tissue previously exposed to pressure may not eliminate all of the previously identified locations of PUR, since some repositioned tissue may remain exposed to pressure at a new location on the support surface.

The present invention provides an improved method for mapping pressure ulcer risk that overcomes drawbacks of prior art methods.

SUMMARY OF THE INVENTION

In accordance with the present invention, there is provided a method for continuously monitoring pressure ulcer risk for a patient positioned on a support surface. The support surface has an associated pressure sensing device for sensing instantaneous pressure at the support surface. The method includes an acquisition of pressure data from the pressure sensing device to generate a two-dimensional instantaneous pressure (IP) map indicative of instantaneous pressure at locations of the support surface. Then a body position model is acquired using the two-dimensional IP map. The body position model includes body parts that are respectively mapped to locations on a pressure ulcer risk map. The method further includes a determination of an accumulated risk in association with each body part. Then the pressure ulcer risk map is displayed in accordance with the accumulated risk. The method additionally includes a comparison of a current body position model to a previous body position model to detect whether there has been a position change of the patient on the support surface. If there is no position change detected, then it is determined that old tissues remains located at an old position. If a new position change is detected, then it is determined that new tissue is located at a new position. If a translation of position is detected, then it is determined that old tissue is located at a new position. If a micro-reposition is detected, then it is determined that new tissue is located at an old position.

In accordance with another aspect of the present invention, there is provided a method for continuously monitoring pressure ulcer risk for a patient positioned on a support surface. The support surface has an associated pressure sensing device for sensing instantaneous pressure at an interface between the support surface and the patient. The method includes a generation of an instantaneous pressure (IP) map from pressure data corresponding with the sensed instantaneous pressure. Then a body position model is generated using data obtained from the IP map. The body position model includes a plurality of body parts. The method further includes a determination of accumulated risk for each of the body parts by accumulating instantaneous pressure over time for each of the body parts. Then a pressure ulcer risk map is generated. The pressure ulcer risk map provides a Boolean indication of whether a body part is at low risk or high risk of developing a pressure ulcer. The pressure ulcer risk map is generated using the accumulated risk for each of the body parts. The body parts are respectively mapped to locations on the pressure ulcer risk map. Then the pressure ulcer risk map is displayed.

In accordance with still another aspect of the present invention, there is provided a method for continuously monitoring pressure ulcer risk for a patient positioned on a support surface. The support surface has an associated pressure sensing device for sensing instantaneous pressure at the support surface. The method includes an acquisition of a two-dimensional instantaneous pressure (IP) map indicative of instantaneous pressure sensed at the support surface. Then a body position model is acquired from the two-dimensional IP map. The body position model includes a plurality of body parts. An accumulated risk is determined for each of the body parts. Then a risk map is displayed in accordance with the accumulated risk.

In accordance with yet another aspect of the present invention, there is provided a method for continuously monitoring pressure ulcer risk for a patient positioned on a support surface. The support surface has an associated pressure sensing device for sensing instantaneous pressure at the support surface. The method includes an acquisition of pressure data from the pressure sensing device to generate a two-dimensional instantaneous pressure (IP) map indicative of instantaneous pressure at a plurality of locations on the support surface. Then a body position model is acquired using the two-dimensional IP map. The body position model includes a plurality of body parts. Then the instantaneous pressures of the two-dimensional IP map are used to determine a three-dimensional body position model. The method further includes a determination of an accumulated risk associated with each body part of the body position model. Then a pressure ulcer risk map is displayed in accordance with the accumulated risk associated with each of the body parts.

An advantage of the present invention is the provision of a PUR mapping method that illustrates PUR for tissue exposed to pressure in a clear and concise manner, thereby allowing medical personnel to act quickly to avoid and treat pressure ulcers.

Another advantage of the present invention is the provision of a PUR mapping method that replaces gradient maps with simple "Boolean" or high contrast PUR maps that allow a clinician to readily identify regions at which there is increased risk of developing pressure related tissue damage and regions at which there is low risk (i.e., little or no risk) of developing pressure related tissue damage.

Still another advantage of the present invention is the provision of a PUR mapping method that conformally maps a three-dimensional patient surface to a two-dimensional support surface.

Still a further advantage of the present invention is the provision of a PUR mapping method that associates PUR with a body part exposed to pressure, and either maintains the associated PUR with the body part when the body part is repositioned to a new location, or performs a washout of the PUR with reperfusion characteristics of the associated patient tissue.

Still another advantage of the present invention is the provision of a PUR mapping method that provides a feed forward predictive PUR map to aide in locating a patient to a position that minimizes the risk of pressure ulcer development.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE INVENTION

Figure 1:
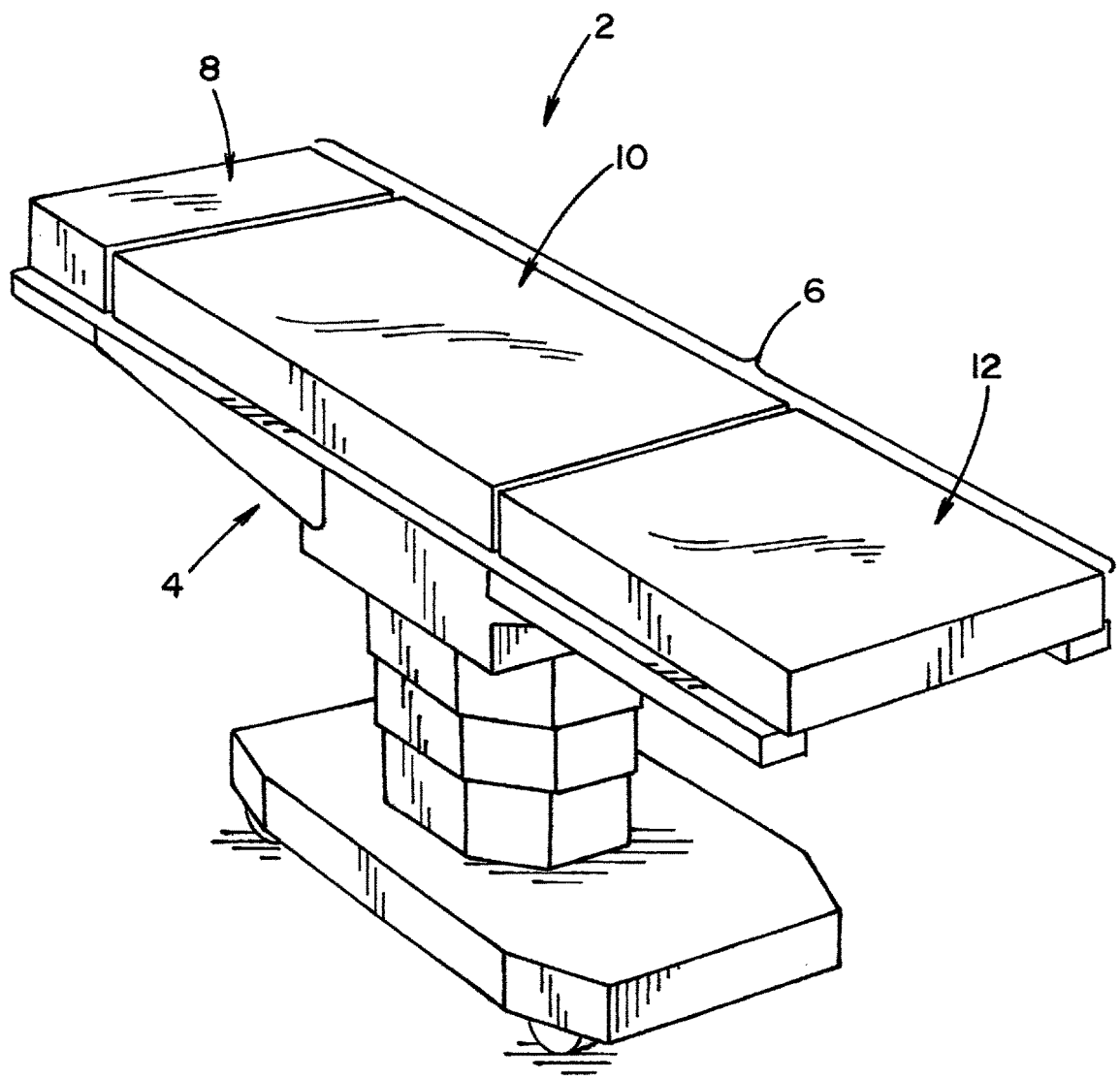
FIG. 1 is a perspective view illustrating a support pad assembly according to an embodiment of the present invention, wherein the support pad assembly is positioned on an example surgical table.

Referring now to the drawings wherein the showings are for the purposes of illustrating embodiments of the invention only and not for the purposes of limiting same, FIG. 1 shows a support pad assembly 6 according to an embodiment of the present invention. In the illustrated embodiment, support pad assembly 6 is positioned on a tabletop 4 of a surgical table 2 to support and cushion a patient that is situated thereon. Support pad assembly 6 has a support surface that is in contact with the patient.

Support pad assembly 6 is generally comprised of one or more support pads according to patient positioning needs. In the illustrated embodiment, support pad assembly 6 is generally comprised of support pads 8, 10, and 12 for respectively supporting and cushioning a head, a torso, and a leg/foot region of a patient.

While support pad assembly 6 is illustrated as being positioned on tabletop 4 of surgical table 2, it will be readily appreciated that support pad assembly 6 may be modified or configured to cushion a patient on any suitable surface known in the art. For example, support pad assembly 6 may be used in connection with surfaces of a hospital bed, an examination table, a mattress, a foam pad, a gurney, and the like.

In addition, support pad assembly 6 may be configured to accommodate various patient positions, including, but not limited to, supine, prone, lateral, lithotomy, sitting, trendelenberg, reverse trendelenberg, split leg, and beach chair. Furthermore, in an alternative embodiment, support pad assembly 6 is comprised of a single support pad sized to cover the entire surface area of tabletop 4. In another alternative embodiment, where tabletop 4 has been modified or expanded to accommodate various patient positions such as those described above, support pad assembly 6 may be modified or configured according to the modification and expansions of tabletop 4.

Figure 2:
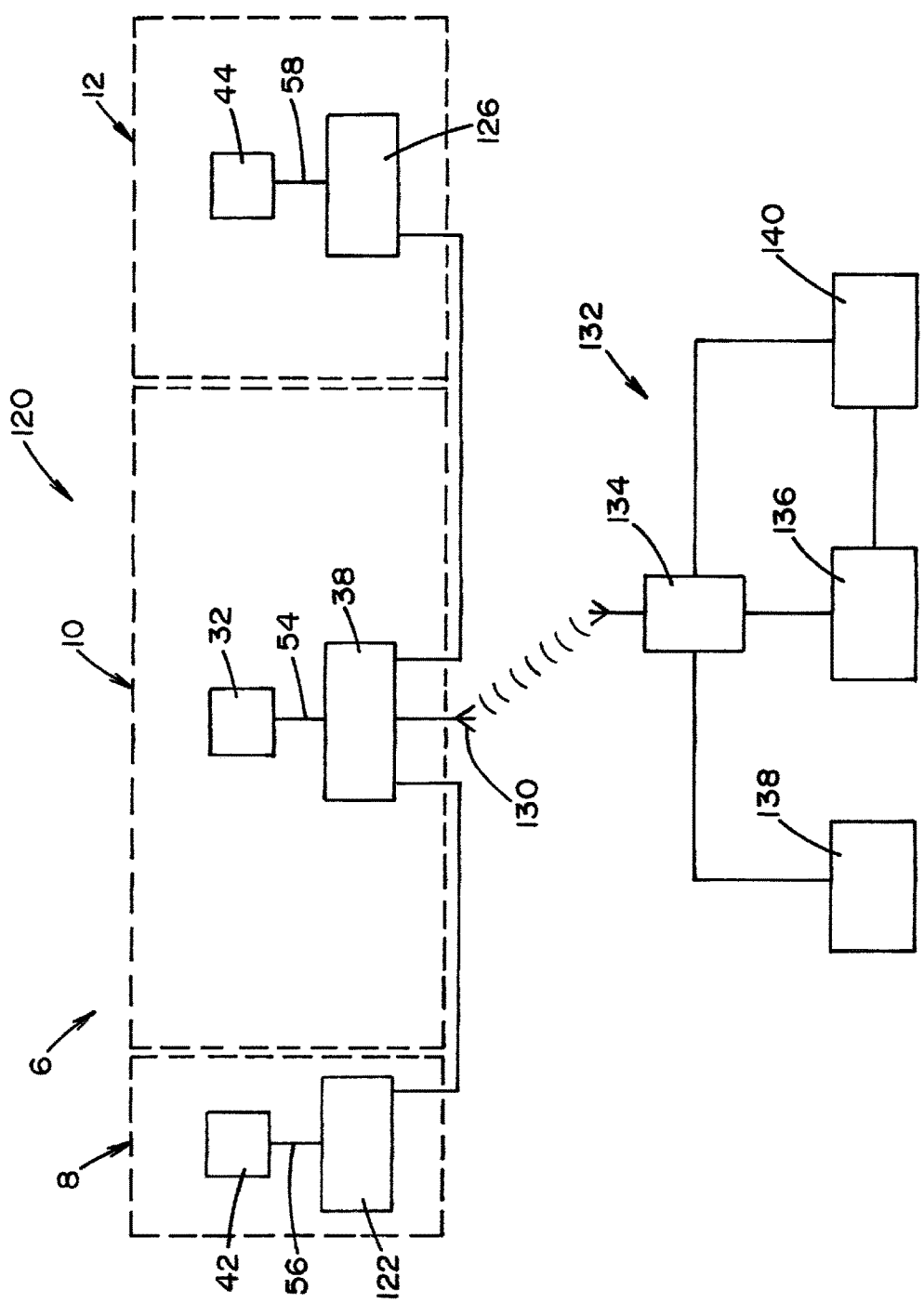
FIG. 2 is a schematic view of a monitoring system, according to an embodiment of the present invention.

FIG. 2 shows a monitoring system 120 according to an embodiment of the present invention. Monitoring system 120 is generally comprised of a data acquisition system 132, at least one wireless communication module 130, respective pressure sensing devices 42, 32, and 44 of support pads 8, 10, and 12, and respective controller units 122, 38, and 126 of support pads 8, 10, and 12.

In the illustrated embodiment, pressure sensing devices 42, 32, and 44 are respectively configured to sense pressure levels to which patient tissue is exposed. In the illustrated embodiment, pressure sensing devices 42, 32 and 44 are comprised of a plurality of pressure sensing elements arranged in a matrix on a flexible substrate, as well known to those skilled in the art. The number of pressure sensing elements in the matrix determines the level of resolution of sensed pressure data.

Controller units 122, 38, and 126 are respectively electrically connected to pressure sensing devices 42, 32, and 44 via respective communication interfaces 56, 54, and 58. Controller units 122, 38, and 126 receive respective pressure data from pressure sensing devices 42, 32, and 44 corresponding to the sensed pressure levels. Controller units 122 and 126 are further configured to relay respective pressure data received from pressure sensing devices 42 and 44 to controller unit 38. The connections between controller units 122, 38, and 126 may be wired or wireless connections.

In the illustrated embodiment, controller unit 38 aggregates the pressure data acquired from pressure sensing devices 42, 32, and 44. Controller unit 38 sends the aggregated pressure data to data acquisition system 132 via wireless communication module 130. It will be appreciated that wireless communication module 130 uses wireless communication protocols well known to those skilled in the art.

In the illustrated embodiment, controller unit 38 serves as a master controller, while controller units 122 and 126 serve as slave controllers. In this respect, controller unit 38 communicates with controller units 122 and 126, and with data acquisition system 132. However, the embodiments described herein are not limited thereto. Further, it will also be appreciated that other suitable arrangements for controller units 122, 38, and 126 may be implemented and will be apparent to those of ordinary skill in the art. For example, controllers 122 and 126 may send data collected from respective pressure sensing devices 42 and 44 directly to data acquisition system 132 via wired or wireless means.

In addition, wireless communication module 130, respective pressure sensing devices 42, 32, and 44 of support pads 8, 10, and 12, and respective controller units 122, 38, and 126 of support pads 8, 10, and 12 may receive power through surgical table 2 or any number of means known to one having ordinary skill in the art.

Data acquisition system 132 is configured to store, display, and process the aggregated pressure data. In the illustrated embodiment, data acquisition system 132 is generally comprised of a processing unit 134, an input unit 136, a data storage unit 138, and a display unit 140. Processing unit 134 receives the aggregated pressure data from controller unit 38 and processes the pressure data, as will be described in detail below. Display unit 140 may include, but is not limited to, a video display, a projector, and a printer. Input unit 136 provides means for the user to input data or instructions. Input unit 136 may include, but is not limited to, a keyboard, a mouse controller, and a touch-screen. Furthermore, it should be appreciated that input unit 136 and display unit 140 may be combined into a touch-screen display unit. Devices corresponding with input unit 136 and display unit 140 are well known to the ordinary skilled artisan.

Manifestations of data acquisition system 132 may be implemented and will be apparent to those of ordinary skill in the art. For example, it will be readily appreciated that data acquisition system 132 may be contained within a personal computing device or distributed over a plurality of computing devices in multiple locations. Furthermore, data acquisition system 132 may advantageously employ any combination of computing devices, user inputs, displays, notification devices, data storage servers, and networking components known to one having ordinary skill in the art.

Acquisition and Mapping of Pressure Data

A patient supported by support pad assembly 6 applies a load thereto. As a result, an interface pressure is applied to patient tissue that is in contact with the support surface of support pad assembly 6. Pressure sensing elements of pressure sensing devices 42, 32, and 44 sense interface pressure levels at various locations of support pad assembly 6. As indicated above, the pressure sensing elements may be arranged in a matrix.

Pressure sensing devices 42, 32, and 44 provide instantaneous pressure data indicative of the sensed interface pressure levels. This pressure data can be represented by an instantaneous pressure (IP) map. The sensed pressure levels are respectively identified on the IP map according to the locations of support pad assembly 6 at which the pressure levels were sensed. It should be noted that raw pressure data may be subject to preprocessing that includes interpolation, filtering, and contrast enhancement.

Figure 3:
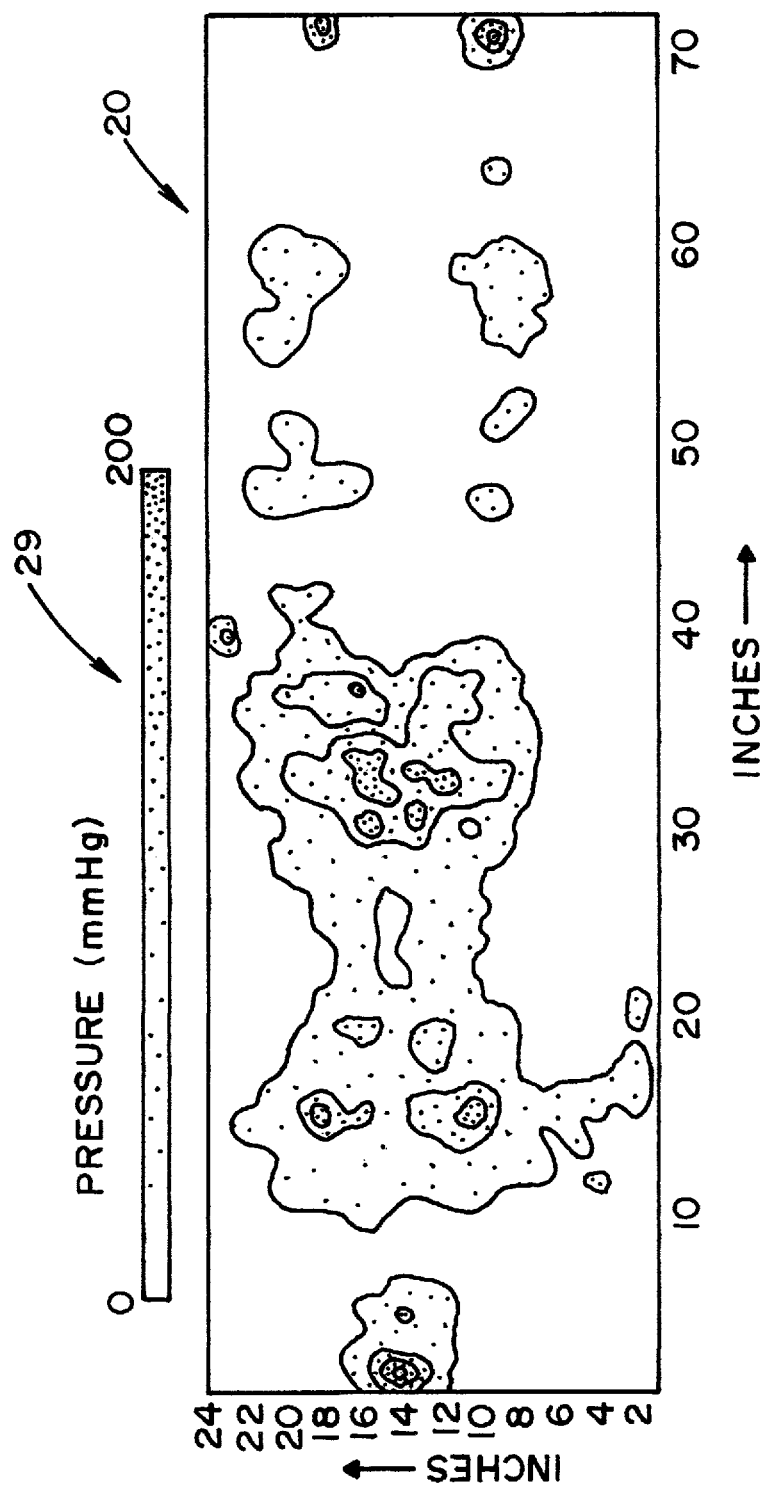
FIG. 3 illustrates an instantaneous pressure map, according to an embodiment of the present invention.

FIG. 3 illustrates an exemplary IP map 20 that is generated by processing unit 134 for a patient supported on support pad assembly 6 in a supine (face up) position. IP map 20 shows the instantaneous pressure at respective locations of support pad assembly 6. The instantaneous pressure shown in IP map 20 is indicative of the interface pressure applied to patient tissue at various regions of the patient's body. A legend 29 identifies the pressure level values shown in IP map 20.

Acquisition of Body Position Model

Figure 4A:
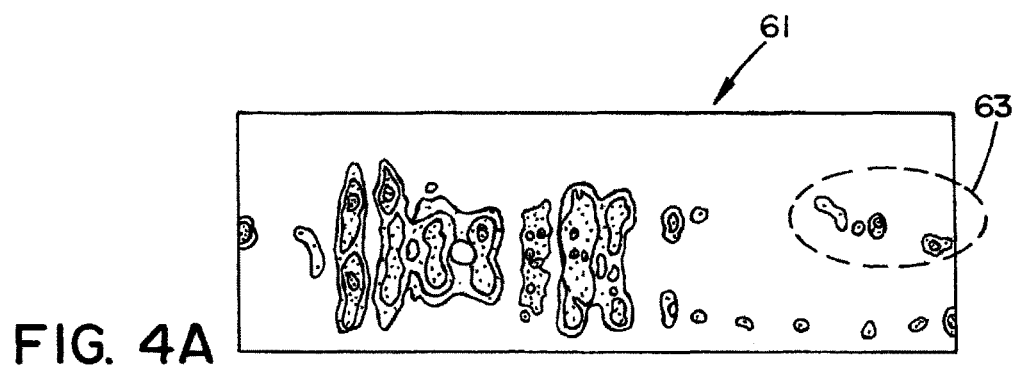
FIGS. 4A and 4B respectively illustrate an instantaneous pressure map and corresponding body position model, according to an embodiment of the present invention.
Figure 4B:
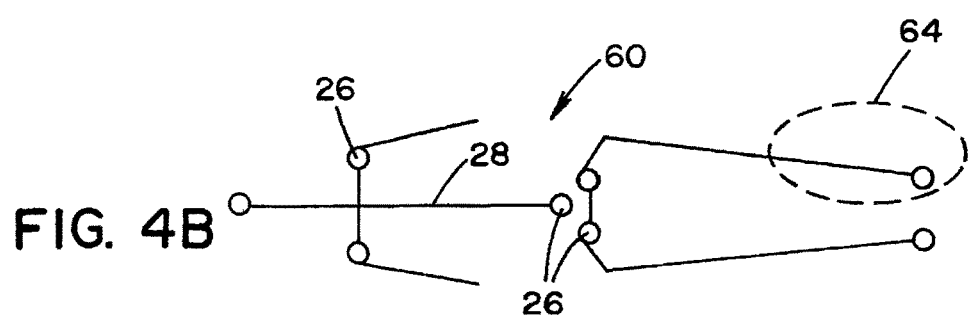
Figure 5A:
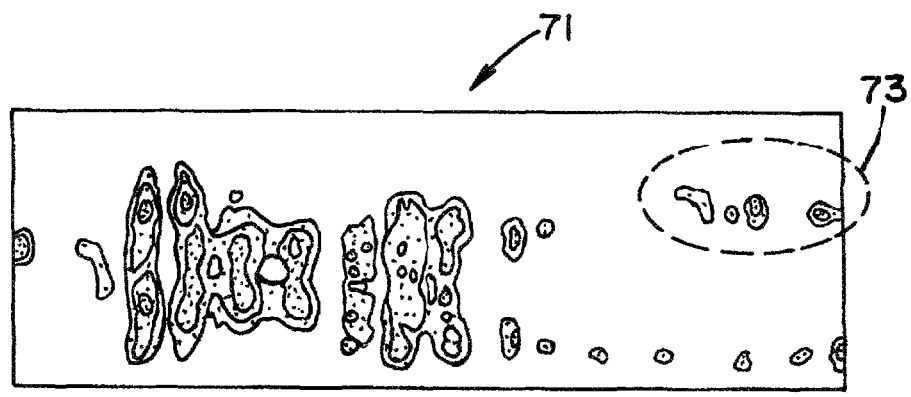
FIGS. 5A and 5B respectively illustrate an instantaneous pressure map and corresponding body position model, according to an embodiment of the present invention.
Figure 5B:
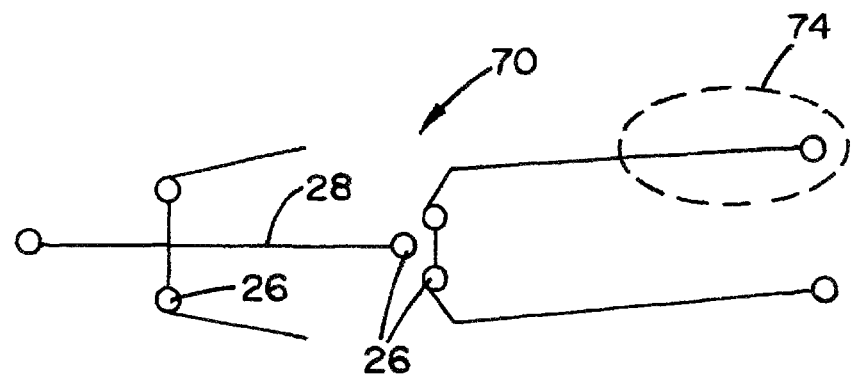
Figure 6A:
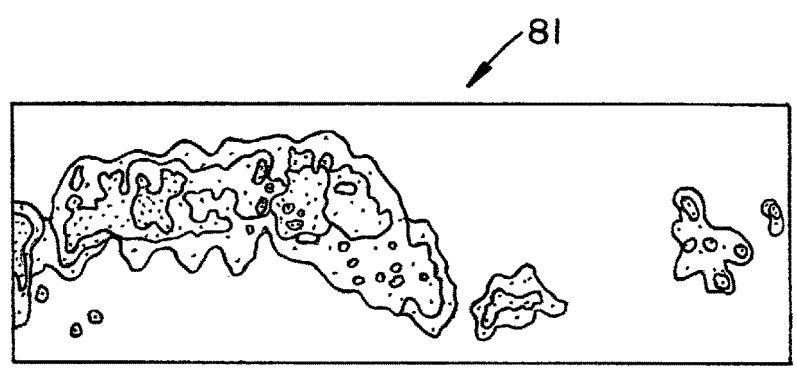
FIGS. 6A and 6B respectively illustrate an instantaneous pressure map and corresponding body position model, according to an embodiment of the present invention.
Figure 6B:
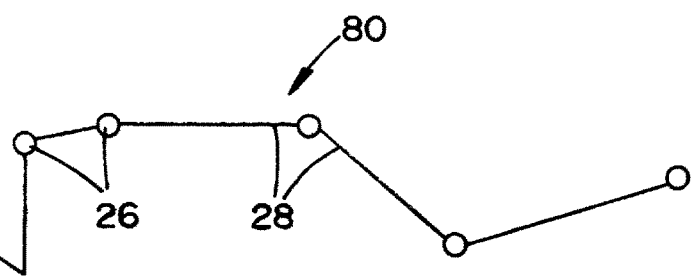

FIGS. 4A, 5A, and 6A respectively show first supine, second supine, and lateral IP maps 61, 71, and 81. FIGS. 4B, 5B and 6B show first supine, second supine, and lateral body position models 60, 70, and 80 that respectively correspond with IP maps 61, 71, and 81.

In the illustrated embodiment, body position models 60, 70, and 80 are respectively acquired from analysis of IP maps 61, 71, and 81. Body position models 60, 70, and 80 are used to model respective positions in which a patient is oriented on support pad assembly 6 (e.g., supine, prone, lateral, lithotomy, sitting, trendelenberg, reverse trendelenberg, and split leg positions). Each body position model 60, 70, and 80 is comprised of a plurality of nodes 26 and a plurality of connectors 28 that connect nodes 26. Nodes 26 correspond with expected acute high pressure areas.

A body position model corresponding to an IP map may be a determined using processing unit 134 to search a library of pre-stored body position models for a body position model that most closely correlates with the IP map. In this respect, a plurality of body position models are developed to represent each of the body positions of interest and are pre-stored in data storage unit 138. Correlation of the IP map with a body position model may be determined by iterating through the pre-stored body position models. This iteration continues until a body position model having a high matching correlation with the IP map is identified. As an alternative to searching the library of pre-stored body position models, a body position model can be located in the library by receiving a user input that identifies the actual patient position.

After a body position model is selected from the library, it is optimized, if necessary. In this respect, the selected body position model is modified to more closely correlate the body position model to the IP map. For example, one or more nodes may be repositioned, and one or more connectors may be repositioned and/or lengthened/shortened.

In the illustrated embodiment, data correlation is used in the process of matching an IP map to a body position model, and in the process of optimizing a body position model. The data correlation process includes identification of symmetrical and asymmetrical regions in a correlation map. For example, symmetry can be identified by maximizing the peak in the center of a bi-fold correlation map. Edge detection, blob recognition, and other well known feature extraction techniques may also be used for matching and optimizing.

It should be appreciated that data correlation processes are well known to those skilled in the art, and thus are not described in detail herein. Furthermore, the body position models illustrated herein are only representative examples of suitable body position models, and are not intended to limit the scope of the present invention.

The nodes and connectors of the body position model are associated with a plurality of body parts (e.g., occiput, shoulder, heel, etc.). These body parts are mapped to locations on a risk map, which is described below.

Accumulated Risk

Risk of pressure ulcer development is generally related to an amount of pressure to which patient tissue is exposed and the time duration over which the exposure occurs. Several pressure ulcer risk curves have been developed that illustrate this relationship, such as, but not limited to, the Reswick and Rogers pressure-time curve. In the region above the curve, the patient tissue is at high risk of developing a pressure ulcer. In the region below the curve, the patient tissue is at low risk (i.e., little or no risk) of developing a pressure ulcer.

Figure 7:
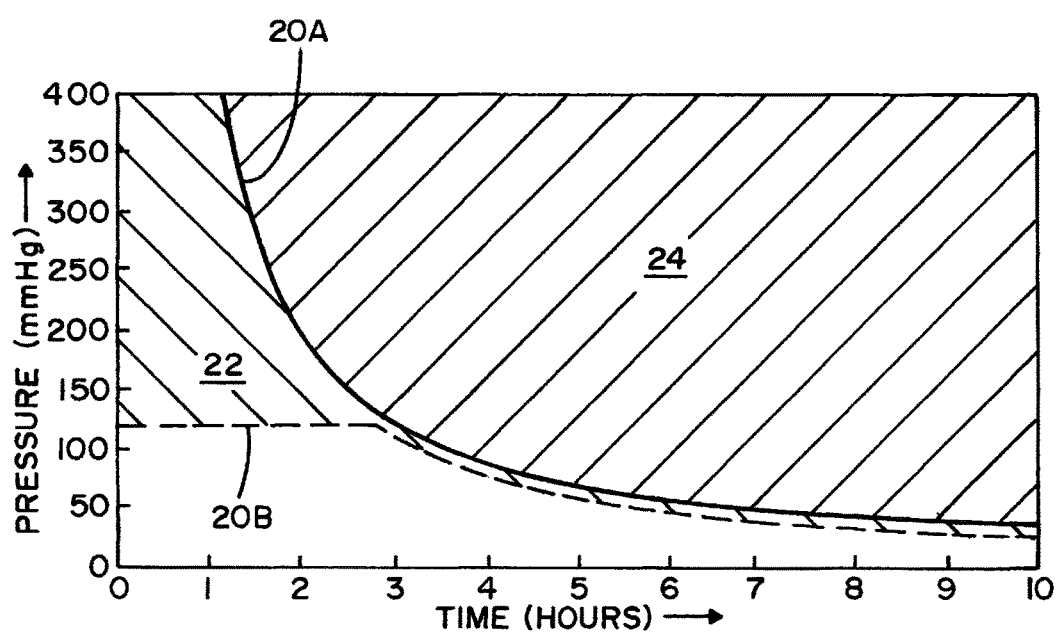
FIG. 7 illustrates examples of standard and modified pressure ulcer risk curves.

Referring now to FIG. 7, there is shown an example pressure ulcer risk curve 20A that is similar to the Reswick and Rogers pressure-time curve. Curve 20A is the boundary between a region 24 at which there is high risk of developing pressure related tissue damage and a region at which there is low risk of developing pressure related tissue damage. Thus, curve 20A defines a risk threshold. For example, patient tissue exposed to 200 mmHg of pressure for less than about 2 hours is at low risk of developing pressure ulcers. However, if the same patient tissue continues to be exposed to 200 mmHg over 2 hours, then the patient tissue would be at high risk of developing pressure ulcers.

Multiple pressure ulcer risk curves may be used in the present invention. For example, pressure ulcer risk curve 20B defines a different boundary between high risk and low risk regions. Ulcer risk curve 20B is more conservative than risk curve 20A, as the high risk region is expanded to include both regions 24 and 22. Risk curve 20B may be more appropriate for a specific patient having a history of pressure ulcers or for body parts that are known to be more susceptible to pressure ulcer development. Accordingly, it is contemplated that different pressure risk curves may be used in connection with different body parts due to differing patient tissue composition.

In accordance with an embodiment of the present invention, a risk function equation (e.g., Equation 1 set forth below) is used to determine an accumulated risk, determine if a risk threshold has been exceeded, and provide a corresponding Boolean risk output of 0 (low risk) or 1 (high risk) indicative of whether the risk threshold has been exceeded. The risk function equation may be adapted for each patient based on assessed risk, and use of evidence-based accepted tools, such as the Braden Scale, Munro Scale, Waterlow Card, or Scott-Triggers. For example, curve 20B could be substituted for curve 20A. The risk accumulates in accordance with the elapsed exposure time and pressure level. In accordance with an embodiment of the present invention, risk is accumulated for individual body parts.

Further, the risk function equation considers the impact of reperfusion on the affected tissue. Reperfusion is the restoration of blood flow to tissue after a period during which blood flow was inhibited or denied. In the illustrated embodiment, when tissue is exposed to interface pressure, blood flow to the exposed tissue is inhibited or denied, thus resulting in risk accumulation. When the tissue is no longer exposed to interface pressure, blood flow is restored to the tissue. In other words, reperfusion occurs.

The risk function equation additionally considers the impact of reperfusion on the affected tissue by introducing a washout term. As used herein, "washout" is the manner for applying the risk reduction effect of reperfusion to the risk function equation. In the illustrated embodiment, when the tissue is no longer exposed to interface pressure, the blood flow that is resumed to the affected tissue serves to feed and clean the tissue. The feeding and cleaning of the tissue serves to progressively reduce the risk of pressure ulcers over time. This progressive reduction in pressure ulcer risk is factored into the risk function equation via "washout".

$$\hat{p}_{i,j}(t) = \alpha \cdot p_{i,j}(t) + (1-\alpha) \cdot \hat{p}_{i,j}(t-1) \qquad \text{Equation 1}$$

$$g_{i,j}(t) = \begin{cases} \gamma & \hat{p}_{i,j}(t) < P_{min} \\ \left(\dfrac{\hat{p}_{i,j}(t) - 11.527 - b}{471.92}\right)^{-3/4}, & \hat{p}_{i,j}(t) \geq P_{min} \end{cases}$$

$$a_{i,j}(t) = \sum_{t=-\infty}^{t_0} d_t / g_{i,j}(t)$$

$$r_{i,j}(t) = \begin{cases} 0, & a_{i,j}(t) < 1 + T_b \\ 1, & a_{i,j}(t) \geq 1 + T_b \end{cases}$$

$i$-row index $j$-column index $p$-pressure (mmHg)

$\alpha$-lowpass filter coefficient $\hat{p}$-pressure limited (mmHg)

$b$-adjustable bias $g$-incremental risk $\gamma$-washout coefficient $dt$-sample time (hr)

$a$-accumulated risk $T_b$-threshold bias $r$-risk output

Row index i and column index j identify a corresponding matrix location of a support surface at which a pressure sensing elements of a pressure sensing device senses an interface pressure. Pressure $p_{i,j}$ represents the interface pressure sensed at a corresponding row and column location of the matrix. Low pass filter coefficient α is used to filter out acutely high pressure $p_{i,j}$ measurements. Pressure $\hat{p}_{i,j}$ represents the sensed pressure when limited by a minimum threshold pressure at which little or no risk accumulation is expected. The term b represents an overall bias applied in order to tailor risk output $r_{i,j}$ for correspondingly located patient tissue or body parts. The term $g_{i,j}$ represents the risk computed for an increment of time.

The term γ represents a washout coefficient, which serves to apply the risk reduction effect of reperfusion to the risk function equation. The term dt represents a sample time for each instantaneous interface pressure $p_{i,j}$ measurement. The term $a_{i,j}$ represents an accumulated risk. $T_b$ represents a bias to the risk threshold that affects the determination of risk output $r_{i,j}$. The bias $T_b$ is applied in order to tailor risk output $r_{i,j}$ for specific areas of patient tissue or specific patient body parts.

It will be appreciated that Risk Function Equation 1 may be modified in accordance with alternative embodiments of the present invention. Moreover, it will be further appreciated by those having ordinary skill in the art that alternative risk function equations can be substituted for Equation 1 described above.

Risk Map

FIGS. 8A-8E illustrate a risk map shown within a body outline 100. The risk map is continuously updated to show regions of increased risk by application of a risk function equation, such as, for example, Equation 1. Different risk curves can be applied to different body parts shown in the risk map to account for differing patient tissue composition. When is it determined for a body part that the amount of risk has accumulated such that a risk threshold has been exceeded, the risk map is updated to display a visual "risk indicator" (e.g., a colored spot) at a location within the body outline corresponding to the body part at high risk. In the illustrated embodiment, the risk map is a "Boolean" map showing regions of either low risk or high risk. The absence of a risk indicator is indicative of low risk. The presence of a risk indicator is indicative of high risk.

Figure 10:
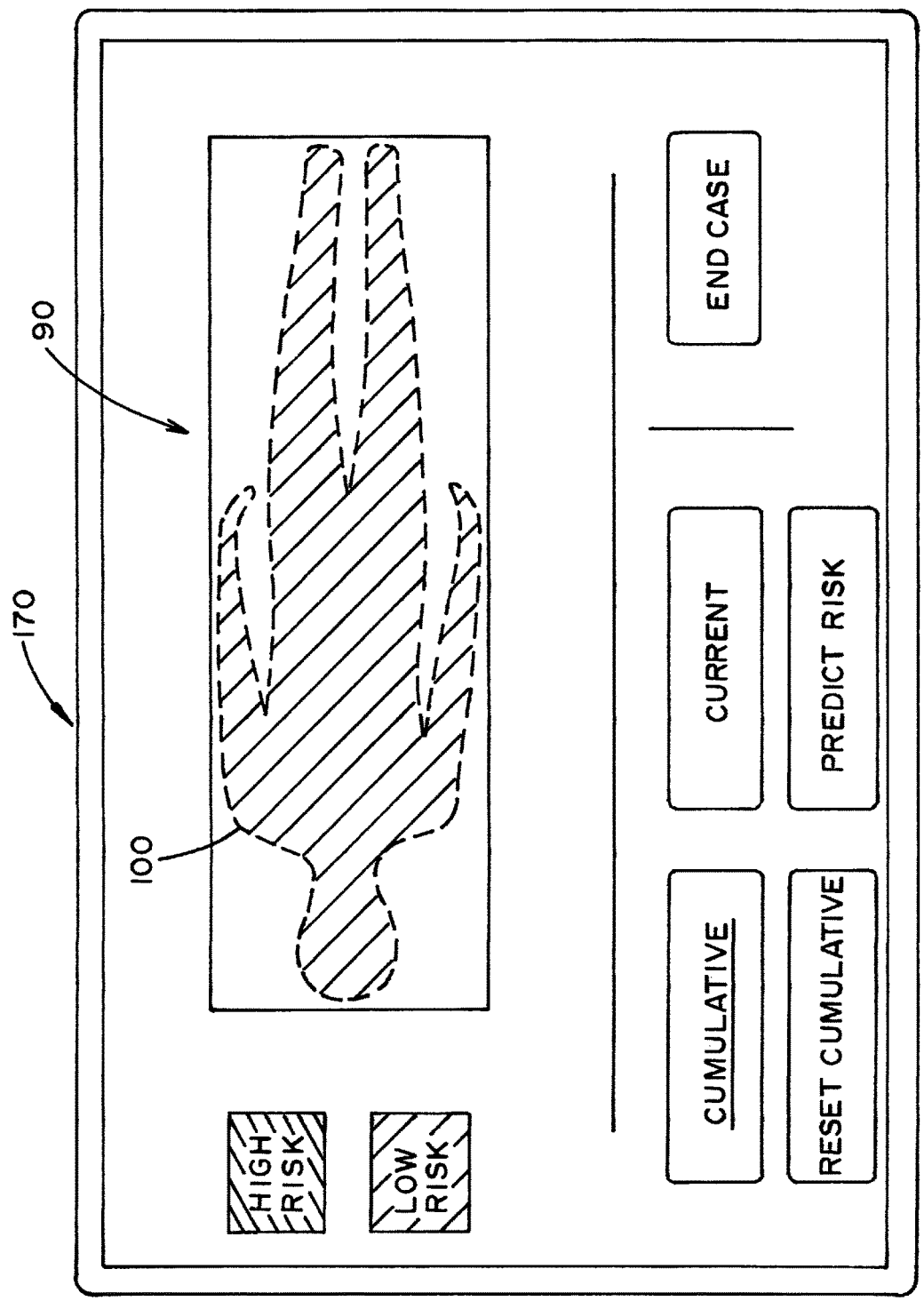
FIG. 10 illustrates a display of a cumulative risk map according to an embodiment of the invention.
Figure 11:
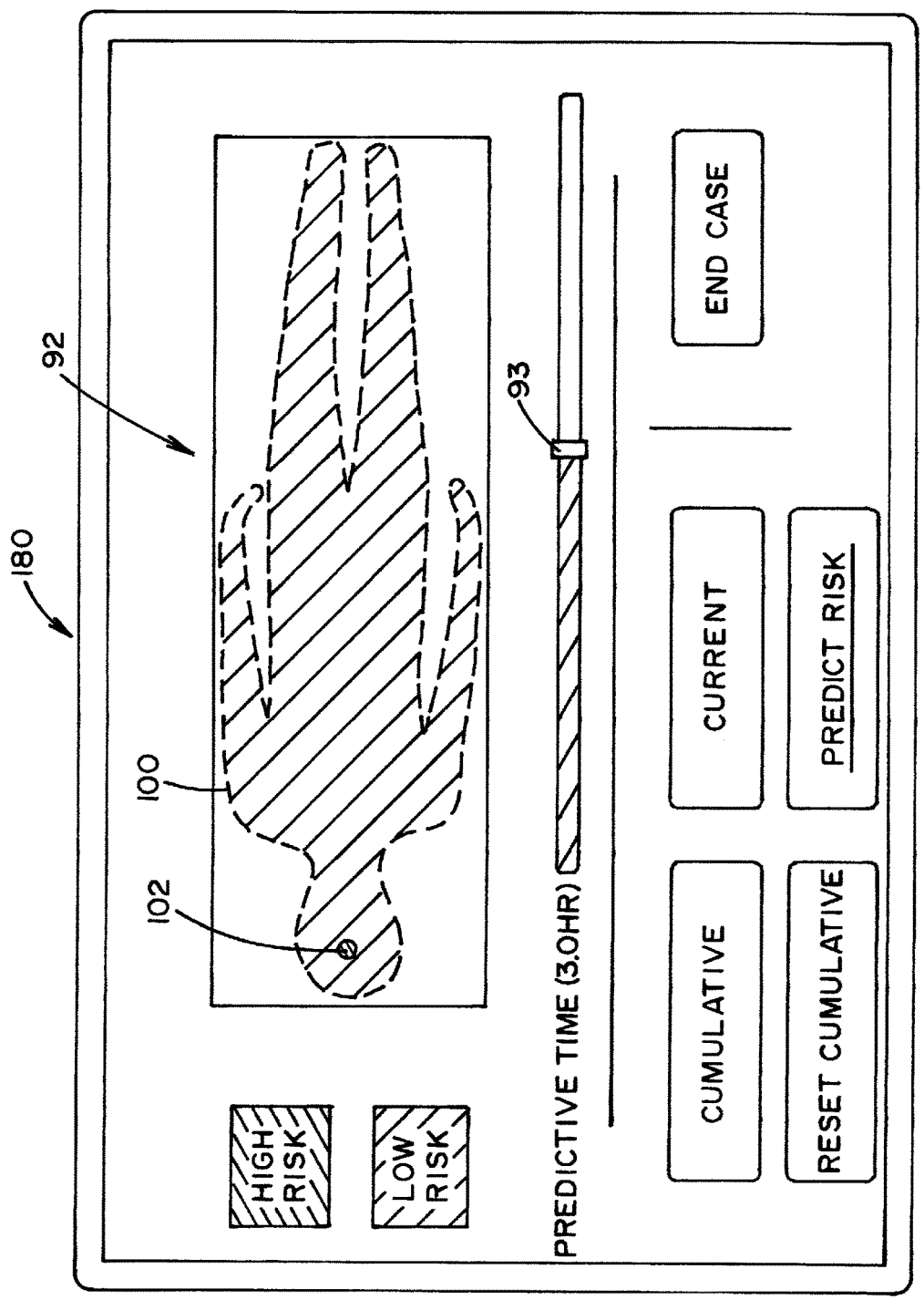
FIGS. 11 and 12 illustrate displays of feed forward predictive risk maps according to an embodiment of the present invention.
Figure 12:
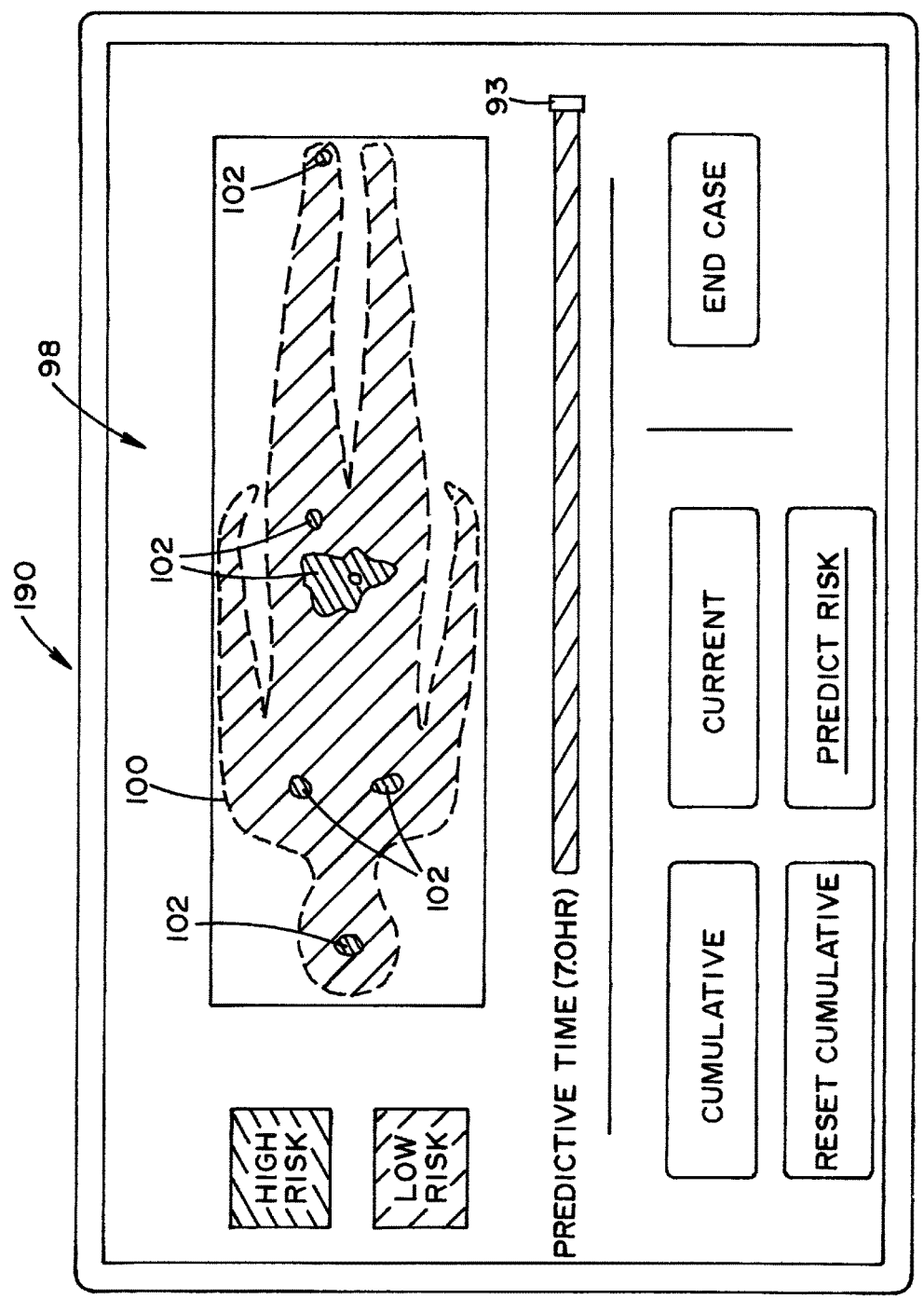

Updating of the risk maps shown in FIGS. 8A-8E will be further described below in connection with a method of mapping pressure ulcer risk. FIG. 10-12 show example touch screen displays 170, 180, and 190 that respectively display risk maps 90, 92, and 98. While FIG. 10 displays risk map 90 as a cumulative risk map, FIGS. 11 and 12 display risk maps 92 and 98 as feed forward predictive risk maps.

Method for Pressure Ulcer Risk Mapping

Figure 9:
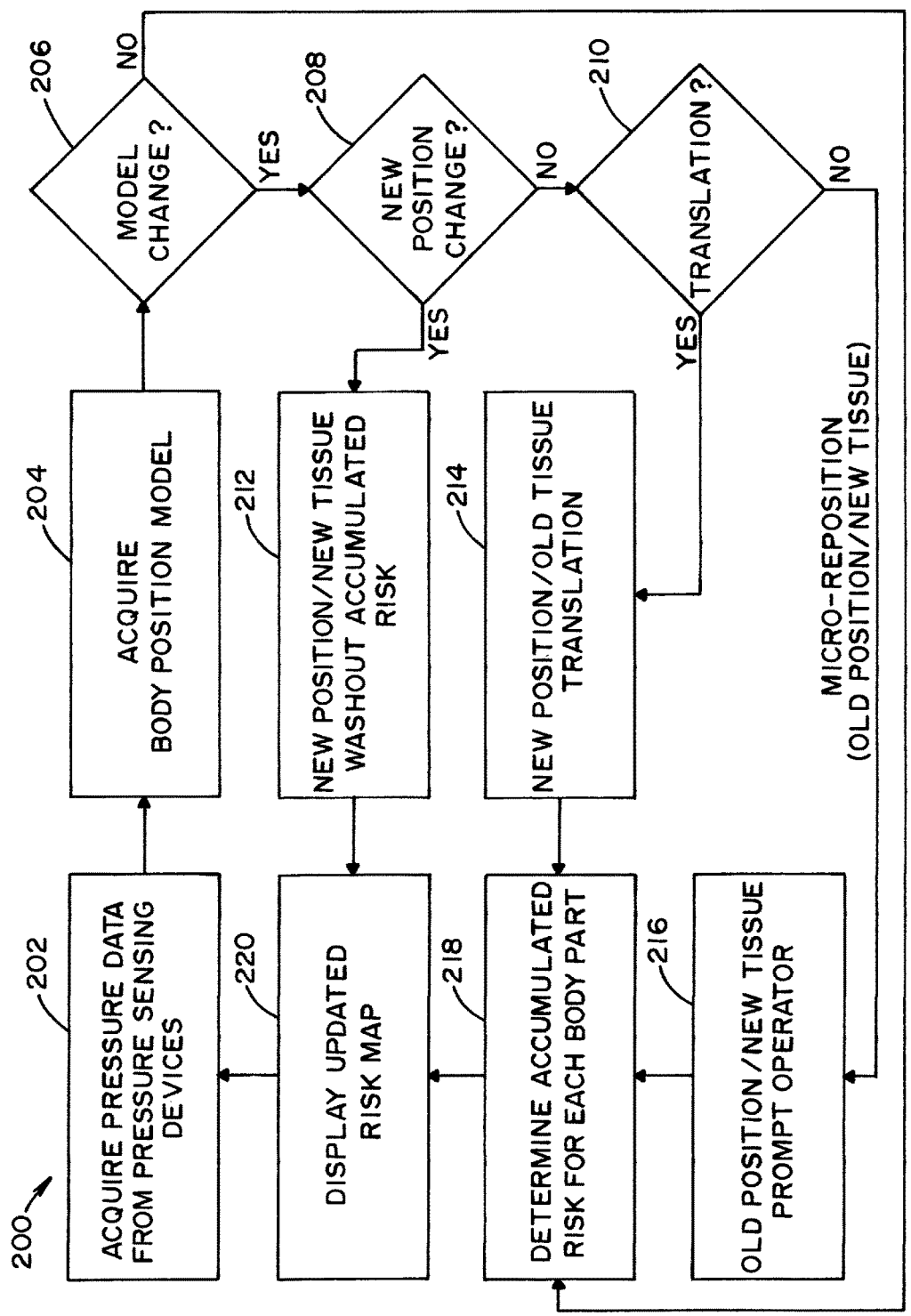
FIG. 9 is a flowchart illustrating a method of mapping pressure ulcer risk according to an embodiment of the present invention.

A pressure ulcer risk mapping method 200 according to an embodiment of the present invention will now be described with reference to FIG. 9. The steps of method 200 may be performed by a controller. The controller may perform the steps automatically or manually according to operator instruction. To initialize method 200, steps 202, 204, 218 and 220 are performed. At step 202, initial pressure data is acquired from pressure sensing devices. An IP map is generated from the pressure data and used to acquire a body position model (step 204), as described in detail above. For example, see IP map 61 (FIG. 4A) and corresponding body position model 60 (FIG. 4B) for a patient in a supine (face up) position on a support surface. Body parts are identified in the body position model. At step 218, an accumulated risk is determined for each body part. Thereafter, the risk map is updated for display at step 220 to complete the initialization of method 200. For example, the risk map may appear as the risk map of FIG. 8A for an exposure time of zero hours.

After initialization of method 200, pressure data is again acquired from pressure sensing devices (step 202) and an IP map is generated. A body position model is acquired using the IP map (step 204). As noted above, body parts are then identified in the body position model. At step 206, it is determined whether there has been a model change between the most recently acquired body position model and the body position model acquired during the previous iteration of method 200. This determination is achieved through a comparison of the body position models.

If it is determined at step 206 that there has been a model change, then it is determined whether the model change is indicative of a new position change (i.e., new position/new tissue) (step 208). A new position change occurs when patient tissue has been removed from contact with the support surface (i.e., old tissue). The old tissue is no longer exposed to interface pressure. In addition, a new position change further includes the positioning of unaffected tissue (i.e., new tissue) on the support surface at a new position to which the old tissue was not previously exposed. For example, a new position change is illustrated by a change in position from a supine position (face up), as shown by IP map 61 (FIG. 4A) and body position model 60 (FIG. 4B), to a lateral position (side position), as shown by IP map 81 (FIG. 6A) and body position model 80 (FIG. 6B).

Thus, in the event of a new position change, the accumulated risk associated with the old tissue begins a progressive reduction (step 212). In other words, reperfusion begins in the old tissue. As a result, the risk map is updated to represent both the washout of the old tissue and the accumulated risk associated with the new tissue located at the new position (step 220).

If it is determined that there has not been a new position change, then it is determined whether a "translation" has occurred at step 210. A translation refers to relocation of a body part from a first location to a second location on the support surface, as indicated by step 214 (i.e., new position/old tissue). For example, a translation of body part(s) is illustrated by a comparison of area 63 of IP map 61 (FIG. 4A) to area 73 of IP map 71 (FIG. 5A). The pressure illustrated in area 63 of IP map 61 is relocated to area 73 of IP map 71. The translation of body part(s) is likewise seen in a comparison of area 64 of body position model 60 (FIG. 4B) with area 74 of body position model 70 (FIG. 5B). If it is determined that there has been a translation, then, at step 218, the accumulated risk for the relocated body part continues to accumulate despite the relocation. The updated risk map is displayed at step 220.

If it is determined at step 210 that there has not been a translation, then it is determined that there has been a micro-reposition of a body part (step 216). A micro-reposition may include a micro-rotation. For example, when a body part (e.g., an arm or leg) is rotated, new tissue is in contact with the support surface at an old position, while old tissue is removed from the old position.

A micro-reposition may be detected by observing a relatively minor difference between the most recently acquired body position model and the body position model acquired during the previous iteration of method 200. If a micro-reposition is detected (i.e., old position/new tissue), then the operator may be prompted at step 216 to indicate whether reperfusion is occurring in the old tissue or risk is continuing to accumulate. Accumulated risk is determined for each body part according to the operator's indication (step 218) and the risk map is updated accordingly (step 220).

Figure 8A:
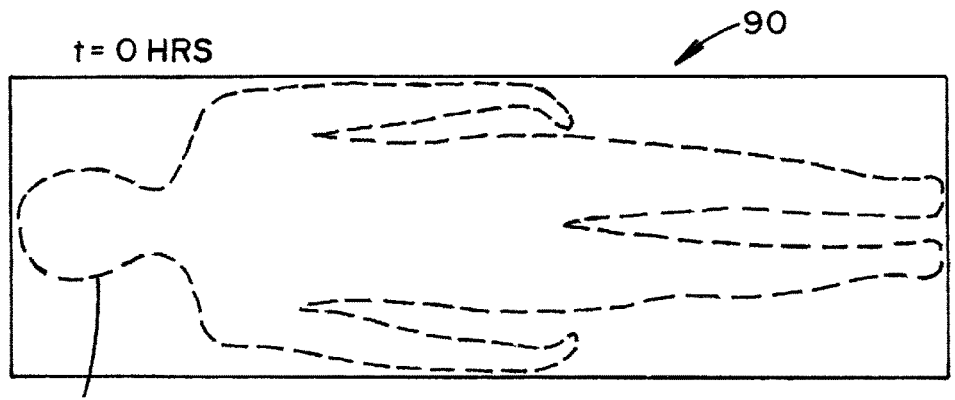
FIGS. 8A-8E are illustrations of cumulative risk maps according to an embodiment of the present invention.
Figure 8B:
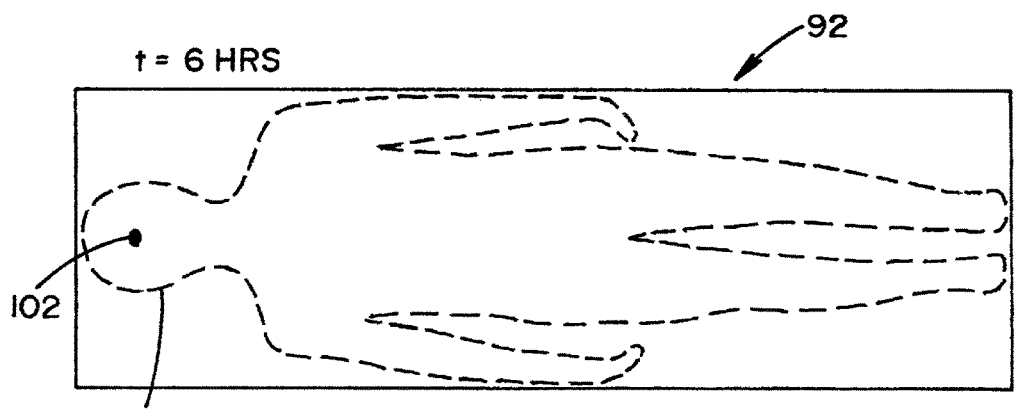
Figure 8C:
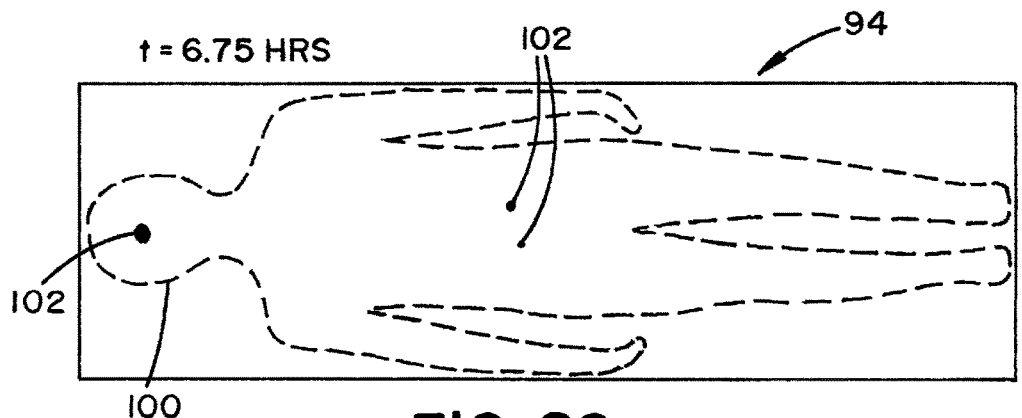
Figure 8D:
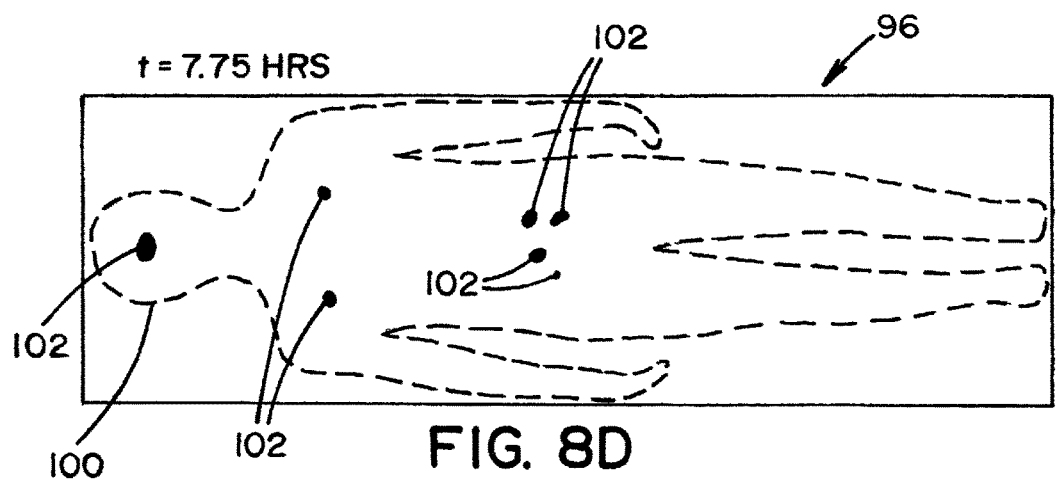
Figure 8E:
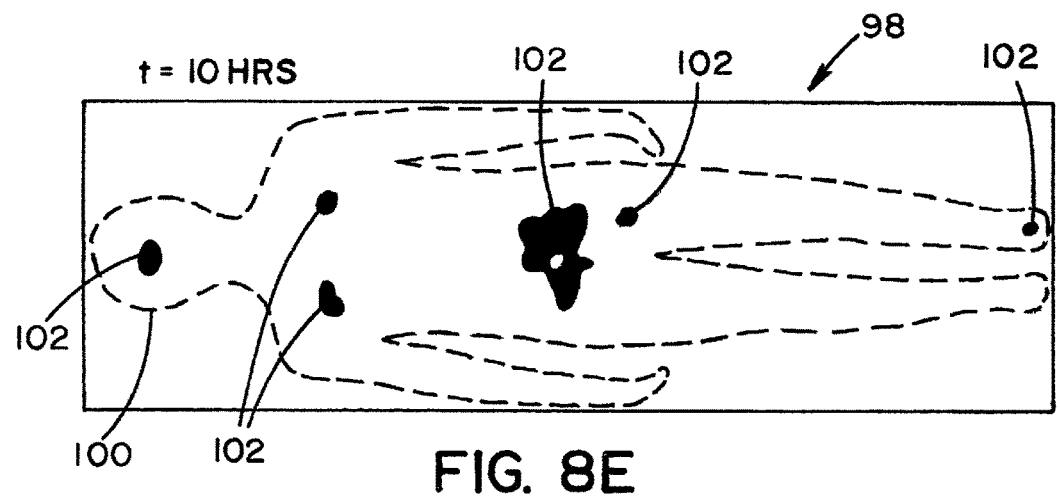

When it is determined at step 218 that the accumulated risk for a body part has exceeded the risk threshold (and thus entered the "high risk" region of a risk curve), then a visual "risk indicator" is displayed on the risk map at a location corresponding to the body part having a high risk of a pressure ulcer. For example, risk map 92 shown in FIG. 8B shows a risk indicator 102 in the head region of body outline 100 at an exposure time of 6 hours. As risk continues to accumulate through additional exposure to pressure, existing risk indicators 102 may expand, and new risk indicators 102 may appear on the risk map. FIG. 8C shows a risk map 94 at an exposure time of 6.75 hours; FIG. 8D shows a risk map 96 at an exposure time of 7.75 hours; and FIG. 8E shows a risk map 98 at an exposure time of 10 hours. In FIGS. 8C-8E it can be seen that existing risk indicators 102 are expanding, and new risk indicators 102 are appearing in association with additional body parts for which the accumulated risk has exceeded the risk threshold.

Feed Forward Predictive Risk Map

Feed forward predictive risk maps will now be described with reference to FIGS. 11 and 12, which respectively illustrate touch screen displays 180 and 190. A pressure ulcer risk curve and a risk function equation, as described above, are used to predict a risk map at a selected predictive time. For example, display 180 (FIG. 11) shows a predictive risk map 92 for 3 hours of continuous exposure to the pressure amounts illustrated in first supine IP map 61. Similarly, display 190 (FIG. 12) shows a predictive risk map 98 for 7 hours of continuous exposure to the pressure amounts illustrated in first supine IP map 61. The predictive time (e.g., expected total surgery time) is selected for display by adjusting sliding bar 93.

Such predictive pressure ulcer risk maps allow an operator to initially position a patient on a support surface to avoid high risk of pressure ulcer development for as long as possible. For example, an operator can use the predictive risk map after initially positioning the patient on a support surface to determine an exposure time and location at which patient tissue may become at a high risk of developing pressure ulcers. The operator may then decide to adjust the patient in an attempt to prolong the length of time patient tissue is at low risk of pressure ulcer development. The operator may continue this process until the patient is positioned optimally on the support surface to avoid increased risk of pressure ulcer development for as long as possible.

Risk Mapping Method

In summary, it will be appreciated that the risk mapping method of the present invention uses a matrix of pressure sensing elements (associated with a support pad providing a patient support surface) to acquire a 2-D pressure map for a patient supported by the support pad. The 2-D pressure map is then used to acquire a 3-D body position model comprised of a plurality of body parts. The 3-D body position model is indicative of the position of the patient supported on the support pad. An accumulated risk is determined for each body part of the 3-D body position model. In this respect, accumulated risk is "mapped" to each of the body parts, regardless of the position of the patient on the support pad. As a result, accumulated risk continues to be accumulated for body parts even when they are relocated to a new position on the support pad. The accumulated risk is used to display a 2-D risk map that provides a Boolean display of risk (i.e., low risk/high risk) for the body parts of the patient.

The foregoing descriptions are example embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method for continuously monitoring pressure ulcer risk for a patient supported on a support surface of a support pad, the method comprising:

positioning a pressure sensing device of a monitoring system in the support pad;

sensing, using the pressure sensing device, interface pressure that is applied by the support surface to an area of the patient supported by a corresponding area of the support surface, the interface pressure affecting tissue associated with the supported area of the patient;

establishing a connection between the pressure sensing device and a controller unit of the monitoring system via a communication interface of the monitoring system;

transmitting instantaneous pressure (IP) data from the pressure sensing device to the controller unit via the communication interface, the IP data identifying amounts of the sensed interface pressure;

sending the IP data from the controller unit to a data acquisition system of the monitoring system;

generating a two-dimensional IP map from the IP data through use of a processing unit of the data acquisition system, the IP map identifying first locations of the support pad at which the interface pressure is sensed and a first amount of the interface pressure sensed at each of the first identified locations;

correlating, via the processing unit, a plurality of body position models stored in a data storage unit of the data acquisition system with the first identified locations of the support pad and the first sensed amount at each of the identified locations to identify, via the processing unit, a first body position model of the body position models;

mapping, using the processing unit, body parts of the identified first body position model to locations on a pressure ulcer risk map corresponding with the first identified locations of the support pad;

determining, using the processing unit, an accumulated risk for each of the mapped body parts of the first body position model in accordance with the first sensed amount at each of the first identified locations;

displaying, via a display unit of the data acquisition system, the pressure ulcer risk map in accordance with the determined accumulated risk;

repeating the sensing, the establishing, the transmitting, the sending, and the generating to identify second locations of the support pad at which the interface pressure is sensed and a second amount of the interface pressure sensed at each of the second identified locations;

correlating, via the processing unit, the plurality of body position models stored in the data storage unit of the data acquisition system with the second identified locations of the support pad and the second sensed amount at each of the second identified locations to identify, via the processing unit, a second body position model of the body position models comparing, using the processing unit, the identified first body position model with the identified second body position model to determine, using the processing unit, whether there has been a position change of the patient on the support surface;

mapping, using the processing unit, body parts of the identified second body position model to locations on the pressure ulcer risk map corresponding with the second identified locations of the support pad;

determining, using the processing unit, a new accumulated risk for each of the mapped body parts of the second body position model in accordance with the second sensed amount at each of the second identified locations; and displaying, via the display unit, an updated pressure ulcer risk map in accordance with the determined new accumulated risk.

2. A method for continuously monitoring pressure ulcer risk as claimed in claim 1, wherein said risk map provides a Boolean indication of whether a respective representation of the mapped body parts of the identified first and second body position models is at low risk or high risk of developing a pressure ulcer.

3. A method for continuously monitoring pressure ulcer risk as claimed in claim 2, wherein the Boolean indication includes (1) a risk indicator displayed at regions of the risk map associated with the high risk and (2) no risk indicator displayed at regions of the risk map associated with the low risk.

4. A method for continuously monitoring pressure ulcer risk as claimed in claim 1, further comprising:

determining, using the processing unit, a feed forward predictive risk for each of the mapped body parts of the patient of the identified second body position model at a selected time by predicting continuous exposure of each of the mapped body parts of the patient of the identified second body position model to the new accumulated risk up to the selected time; and displaying, using the display unit, a map of the determined feed forward predictive risk for each of the mapped body parts of the patient of the identified second body position model.

5. A method for continuously monitoring pressure ulcer risk as claimed in claim 1, wherein the position change is defined by:

removal of the supported area of the patient identified in the first body position model from the corresponding area of the support surface in the second body position model; and support of a new area of the patient, which was not identified in the first body position model and is identified in the second body position model, by a new corresponding area of the support surface that is different from the corresponding area of the support surface at which the area of the patient identified in the first body position model was supported.

6. A method for continuously monitoring pressure ulcer risk as claimed in claim 5, wherein, when the processing unit determines that the position change has taken place, before the displaying of the updated pressure ulcer risk map, the pressure ulcer risk map is updated to represent a washout of the accumulated risk associated with the affected tissue associated with the removed area of the patient according to reperfusion of the affected tissue.

7. A method for continuously monitoring pressure ulcer risk as claimed in claim 5, further comprising, when the processing unit determines that the position change has not taken place:

determining, using the processing unit, whether a translation has taken place, the translation being defined by relocation of the supported area of the patient identified in the first body position model from the corresponding area of the support surface to a second area of the support surface.

8. A method for continuously monitoring pressure ulcer risk as claimed in claim 7, wherein, when the processing unit determines that the translation has taken place, the pressure ulcer risk map is updated to illustrate accumulated risk of the relocated area of the patient at the second area of the support surface before the determining of the new accumulated risk.

9. A method for continuously monitoring pressure ulcer risk as claimed in claim 7, wherein, when the processing unit determines that the translation has not taken place, the processing unit determines that a micro-repositioning of one or more of the mapped body parts of the identified first body position model occurred, the micro-repositioning being defined by support of the new area of the patient corresponding by the corresponding area of the support surface at which the corresponding area of the patient identified in the first body position model was supported, and wherein, when the processing unit determines that the corresponding area of the patient identified in the first body position model has been removed from contact with the support surface in the second body position model, before the determining of the new accumulated risk, the pressure ulcer risk map is updated to represent a washout of the accumulated risk associated with the affected tissue of the removed corresponding area of the patient according to reperfusion of the affected tissue.

10. A method for continuously monitoring pressure ulcer risk for a patient supported on a support surface of a support pad, the method comprising:

positioning a pressure sensing device of a monitoring system in the support pad;

sensing, using the pressure sensing device, interface pressure that is applied by the support surface to an area of the patient supported by a corresponding area of the support surface, the interface pressure affecting tissue associated with the supported area of the patient;

transmitting instantaneous pressure (IP) data from the pressure sensing device to a data acquisition system of the monitoring system, the IP data identifying amounts of the sensed interface pressure;

generating a two-dimensional IP map from the IP data through use of a processing unit of the data acquisition system, the IP map identifying first locations of the support pad at which the interface pressure is sensed and a first amount of the interface pressure sensed at each of the first identified locations;

correlating, via the processing unit, a plurality of body position models stored in a data storage unit of the data acquisition system with the first identified locations of the support pad and the first sensed amount at each of the first identified locations to identify, via the processing unit, a first body position model of the body position models;

mapping, using the processing unit, body parts of the identified first body position model to locations on a pressure ulcer risk map corresponding with the first identified locations of the support pad;

determining, using the processing unit, an accumulated risk for each of the mapped body parts of the first body position model in accordance with the first sensed amount at each of the first identified locations;

displaying, via a display unit of the data acquisition system, the pressure ulcer risk map in accordance with the determined accumulated risk;

repeating the sensing, the establishing, the transmitting, the sending, and the generating to identify second locations of the support pad at which the interface pressure is sensed and a second amount of the interface pressure sensed at each of the second identified locations;

correlating, via the processing unit, the plurality of body position models stored in the data storage unit of the data acquisition system with the second identified locations of the support pad and the second sensed amount at each of the second identified locations to identify, via the processing unit, a second body position model of the body position models;

comparing, using the processing unit, the identified first body position model with the identified second body position model to determine, using the processing unit, whether there has been a position change of the patient on the support surface;

mapping, using the processing unit, body parts of the identified second body position model to locations on the pressure ulcer risk map corresponding with the second identified locations of the support pad;

determining, using the processing unit, a new accumulated risk for each of the mapped body parts of the second body position model in accordance with the second sensed amount at each of the second identified locations; and displaying, via the display unit, an updated pressure ulcer risk map in accordance with the determined new accumulated risk.

* * * * *